United States Patent
Jeannin

(10) Patent No.: US 8,840,331 B2
(45) Date of Patent: Sep. 23, 2014

(54) KIT FOR TOPICAL APPLICATION OF MEDICATION

(75) Inventor: Lionel Jeannin, Choisy (FR)

(73) Assignee: Novartis AG, Basel (CH)

( * ) Notice: Subject to any disclaimer, the term of this patent is extended or adjusted under 35 U.S.C. 154(b) by 768 days.

(21) Appl. No.: 12/937,763

(22) PCT Filed: May 25, 2009

(86) PCT No.: PCT/EP2009/056265
§ 371 (c)(1),
(2), (4) Date: Oct. 14, 2010

(87) PCT Pub. No.: WO2009/144181
PCT Pub. Date: Dec. 3, 2009

(65) Prior Publication Data
US 2011/0065732 A1   Mar. 17, 2011

Related U.S. Application Data

(60) Provisional application No. 61/056,043, filed on May 26, 2008.

(51) Int. Cl.
*A46B 11/00* (2006.01)
*B65D 69/00* (2006.01)
*A61M 35/00* (2006.01)

(52) U.S. Cl.
CPC .................................. *A61M 35/003* (2013.01)
USPC ............ 401/123; 401/130; 206/570; 604/289

(58) Field of Classification Search
USPC .............. 401/123, 130; 514/263.37; 206/570, 206/572; 604/289; 132/320
See application file for complete search history.

(56) References Cited

U.S. PATENT DOCUMENTS

| | | | |
|---|---|---|---|
| 2,099,030 A * | 11/1937 | Morrison | 427/274 |
| 3,759,375 A * | 9/1973 | Nappi | 206/362 |
| 5,231,538 A | 7/1993 | Anderson | |
| 5,660,273 A * | 8/1997 | Discko, Jr. | 206/229 |
| 5,765,573 A | 6/1998 | Gueret | |
| 6,039,053 A * | 3/2000 | Turrentine | 132/320 |
| 6,116,414 A * | 9/2000 | Discko, Jr. | 206/229 |
| 6,211,243 B1 | 4/2001 | Johnson | |
| 6,254,294 B1 | 7/2001 | Muhar | |
| 6,372,313 B1 * | 4/2002 | D'Alessio et al. | 428/34.1 |
| 6,414,032 B1 * | 7/2002 | Johnson | 514/634 |
| 6,929,475 B1 * | 8/2005 | Dragan | 433/89 |
| 6,960,040 B2 * | 11/2005 | D'Alessio et al. | 401/125 |
| 7,186,046 B2 * | 3/2007 | Kauffmann et al. | 401/132 |

(Continued)

FOREIGN PATENT DOCUMENTS

| | | |
|---|---|---|
| EP | 1405579 | 4/2004 |
| GB | 2311726 | 10/1997 |

(Continued)

*Primary Examiner* — David Walczak
*Assistant Examiner* — Jennifer C Chiang
(74) *Attorney, Agent, or Firm* — Larson & Anderson, LLC

(57) ABSTRACT

The application describes a convenient portable kit for the application of topical medications. The kit can be used, for example, as a convenient system for application of cold sore medication. The kit includes a container for a quantity of fluid medication sufficient for several treatments together with a plurality of applicators for said medicine. The applicators are specially designed to apply the medicine accurately and with minimal pain.

26 Claims, 3 Drawing Sheets

(56) References Cited

U.S. PATENT DOCUMENTS

| | | |
|---|---|---|
| 8,181,770 B2 * | 5/2012 | Allard et al. ............ 198/706 |
| 2002/0004063 A1 | 1/2002 | Zhang |
| 2004/0026282 A1 | 2/2004 | D'Alessio et al. |
| 2006/0135464 A1 | 6/2006 | Johnson |
| 2007/0181143 A1 * | 8/2007 | Montoli ............ 132/320 |
| 2008/0072432 A1 | 3/2008 | Teys et al. |

FOREIGN PATENT DOCUMENTS

| | | |
|---|---|---|
| GB | 2460479 A * | 12/2009 |
| WO | WO96/03326 | 2/1996 |
| WO | 9824501 | 6/1998 |
| WO | 0012411 | 3/2000 |
| WO | 0122907 | 4/2001 |
| WO | 2004087002 | 10/2004 |
| WO | 2007066149 A | 6/2007 |

* cited by examiner

KIT FOR TOPICAL APPLICATION OF MEDICATION

BACKGROUND OF THE INVENTION

This application relates to a kit for topical application of medications, for example for the treatment of cold sores.

A cold sores, sometimes called a "fever blister," is a blister or sore which usually appears on the outside of the lips or mouth. It is different from a canker sore, which appears inside the mouth. Cold sores are caused by a virus and are considered a medical condition. Cold sores are usually caused by the herpes simplex virus type 1 (HSV-1). This virus is part of the same family that causes chickenpox, shingles (herpes zoster), and genital herpes (HSV-2).

Cold sores can be different for each person, but, in general, an outbreak lasts about 7 to 10 days and occurs 3 or 4 times a year. During this time, the pain associated with the cold sore can be intense. In addition, cold sores are very contagious and can be spread through physical contact.

Treatment for cold sores can be in the form of oral antiviral medications, but is more commonly in the form of a topical antiviral medication, generally in the form of a cream or ointment. Such medications are available for purchase over-the-counter, without a prescription. Common active ingredients in such medications include, without limitation penciclavir (sold under tradenames Vectavir, Fenestil Pencivir and Denivir, and acyclovir (sold under the tradename Zovirax). Other known antiviral agents which have been used topically and which exhibit an inhibitory effect against HSV in vitro, are for example adenine arabinoside (ara-A, vidarabine), arabinosyladenine-monophosphate (ara-AMP), lobucavir (bishydroxymethylcyclobutylguanine, BHCG), brivudine (bromovinyldeoxyuridine, BVDU), desciclovir, famciclovir, cidofovir (HPMPC, GS504), idoxuridine, netivudine (zonavir, BW882C87), PAA (phosphonoacetate), PFA (phosphonoformate), sorivudine (brovavir, BV-araU), trifluridin (trifluorothymidine, TFT), tromantadine, valacyclovir, virend, 1-docosanol (lidakol), 348U87, 2242 (2-amino-7-(1, 3-dihydroxy-2-propoxymethyl)purine), HOE 961, civamide (capsaicin), PMEA (9-(2-phosphonylmethoxyethyl)adenine), peptide T, BILD 1263, CRT.

Because of the highly contagious nature of the virus that causes cold sores, persons with cold sores are warned against kissing others, or touching the cold sores. It is therefore surprising that instructions accompanying many over-the counter products direct the user to "squeeze a small amount onto your finger and apply to the affected area." In some instances, users are directed to wear a glove or a finger cot or use an applicator (e.g. cotton swab) when applying the topical treatment. These conflicting instructions and the extra effort required to use a glove may result in individuals not applying the medication with the recommended frequency (usually every two to three hours) or for the recommended duration (usually 7 days). Cotton swabs may result is fibers being trapped in the cold sore.

Notwithstanding the inadequacy of existing methods for application of topical antiviral medications, there are few if any improvements in this area. U.S. Pat. No. 6,211,243 discloses an applicator for cold sore medication which has an absorbent, agitation pad, that is abutted against a frangible reservoir. The pad is a cluster of fibers or bristles which are able to hold the treatment composition and abrade disordered tissue. It appears therefore that the intent of this applicator is to use the same applicator for multiple uses (thereby creating a risk of reinfection or transfer to others) and to scrub the topical agent into the cold sore, a process that would cause pain. US Patent Publication No. 2008/0072432 discloses a "dispensing utensil" which can be used to store and dispense cold sore medication. However, the implement or tool used for this application is an applicator pad or brush. Thus, this is also an applicator for multiple uses with its attendant problems.

In short, there remains a need for a product that facilitates easy use of topical cold sore medications, with limited pain and reduced risk of reinfection or transfer of infection to others. It is an object of the present invention to provide such a product.

SUMMARY OF THE INVENTION

The present invention provides a kit for the treatment of medical conditions requiring topical application of a medication. The kit comprises a case having disposed therein:

(a) a container of the medication, wherein the medication is in a fluid form and wherein the container contains sufficient medication for a plurality of applications; and (b) a plurality of applicators each integrally formed from a resilient material, wherein each applicator comprises a handle portion and a flattened blade portion connected by a neck portion, said neck portion being thinner in cross section in at least one dimension than the handle portion and the blade portion such that the flattened blade portion can be deflected during use, and wherein the flattened blade portion has a surface that does not absorb the medication.

DETAILED DESCRIPTION OF THE INVENTION

Figure 1:
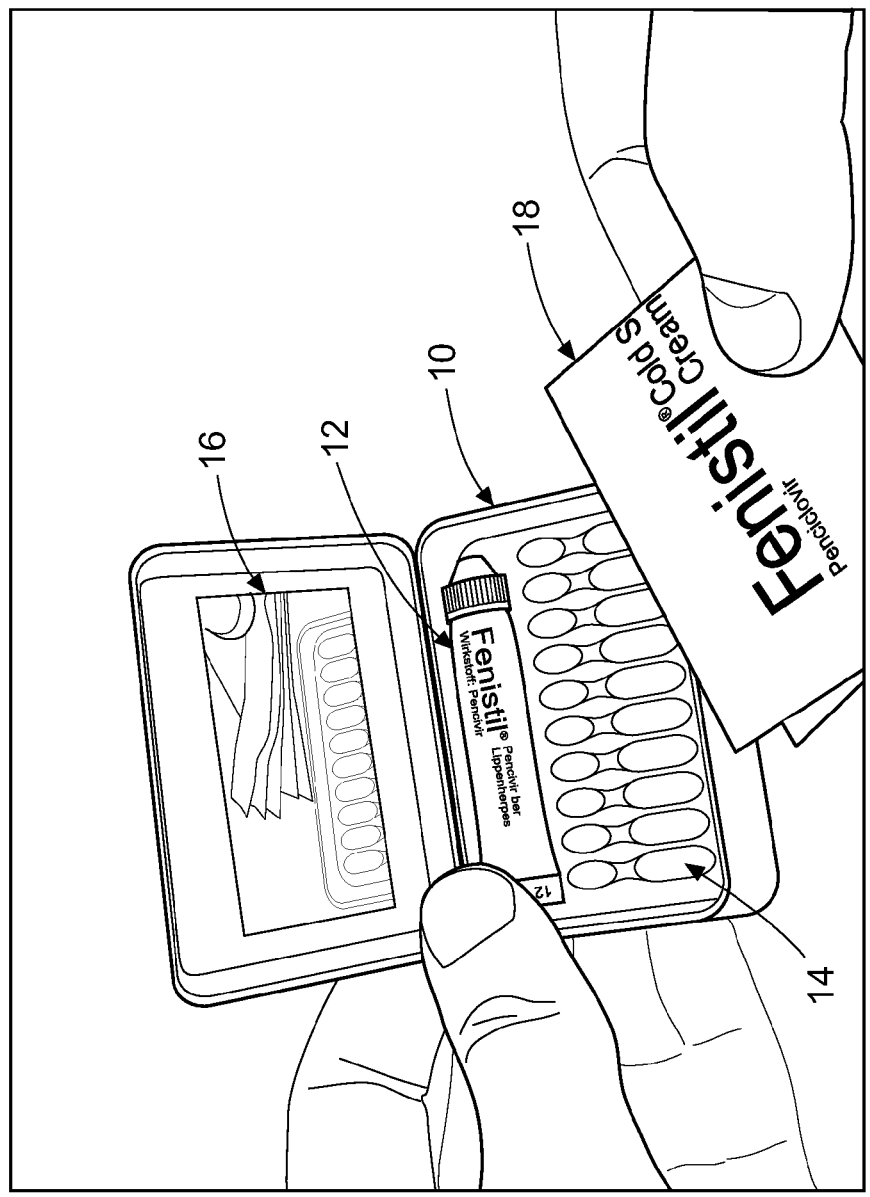
FIG. 1 shows a perspective view of a kit in accordance with the invention.

The present invention provides a kit for the treatment of medical conditions requiring topical application of a medication. FIG. 1 shows a perspective view of a kit in accordance with the invention. The kit has a case 10, a container of the medication 12 and a plurality of applicators 14. Optionally, the kit may also include a mirror 16, and be able to receive printed instructions for use 18 within the case 10. The container of medication contains enough of the medication for a plurality of treatments, for example enough for one entire course of recommended treatment. The numbers of the applicators in the kit and the number of treatments are preferably the same.

Figure 2:
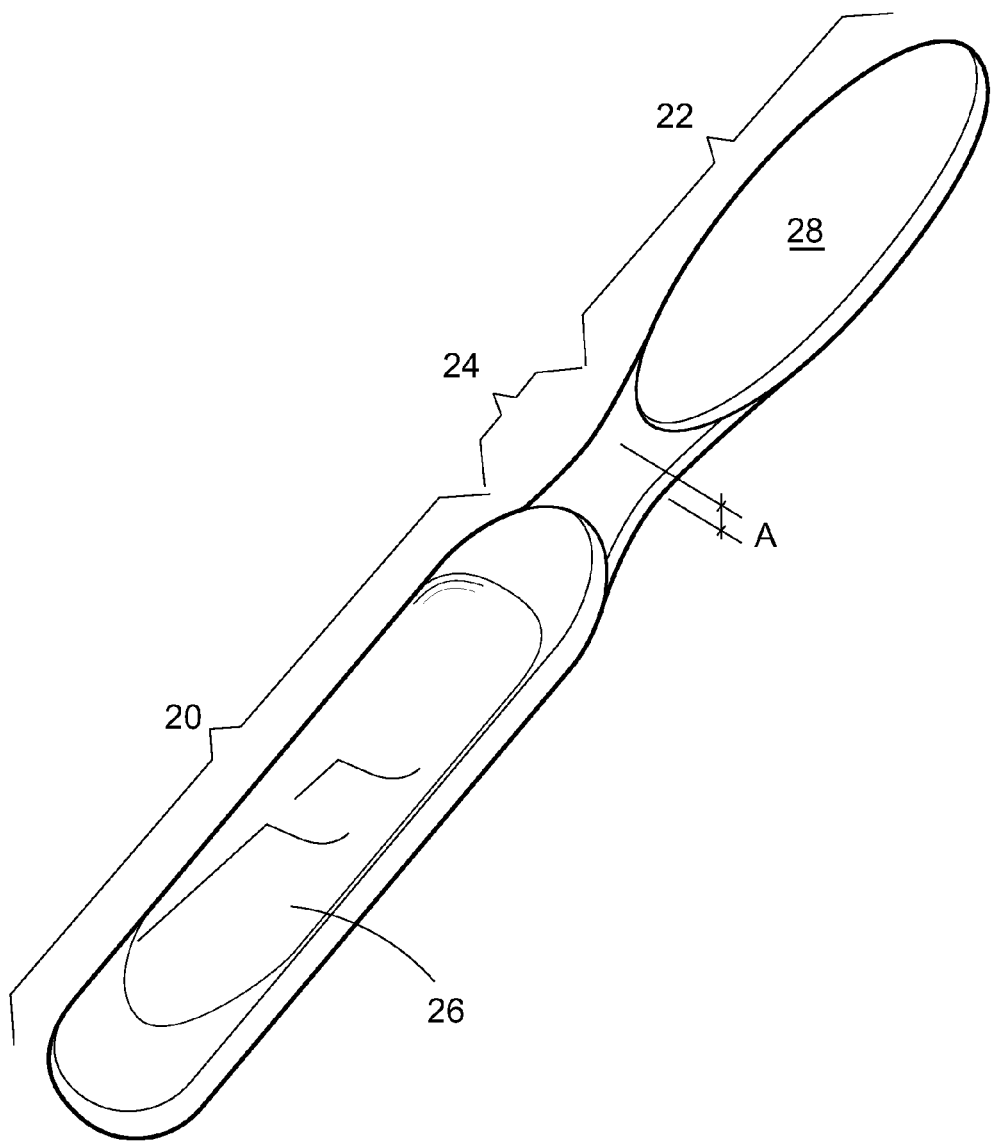
FIG. 2 shows an embodiment of an applicator useful in the kit of the invention.

FIG. 2 shows an embodiment of an applicator useful in the kit of the invention. The applicator comprises an integrally formed handle portion 20 and a flattened blade portion 22 connected by a resilient neck portion 24. The term "integrally formed" means that the applicator is formed from a single piece of shaped material, for example from a molded plastic material.

The handle portion 20 in FIG. 1 has a generally rectangular cross section and has an optional thumb depression 26 formed therein to assist a user in grasping the applicator. The overall shape of the handle portion 20 is, however, a matter of design choice. Thus, the handle portion 20 could have a circular or oval cross section, or a more square cross section and might have raised ridges in place of the thumb depression.

The flattened blade portion 22 is the part of the applicator to which the medication is applied. As shown, this portion has a generally flat top surface 28. The opposing surface (not shown) may also be flat or is may be rounded or have aesthetic features as a design choice. Thus, the term "flattened blade portion" refers to a part of the applicator having at least one generally flat surface 28 to which the medication is applied. The reverse surface may be flat, or may have a curved or decorative surface.

The neck portion 24 is a region of reduced cross sectional height disposed between the flattened blade and the handle. In particular, the cross sectional height A in FIG. 2 is reduced relative to the cross sectional height of the handle and the blade. The neck 24 may also have a reduced cross sectional width if desired. The purpose of the reduction in cross sectional height is to provide the applicator with a resilient flexibility, so that it may bend in the region of the neck when in use. Since cold sores are frequently quite painful, applying medication with a rigid applicator would increase the risk of discomfort, and thus increase the likelihood of non-compliance with the treatment regimen. By reducing the cross sectional height of the neck portion, the applicator has a softer, gentler touch, thus reducing the likelihood of discomfort.

The dimensions of applicator are not critical, but represent a balancing of several concerns. It is desirable for the case (which can be made from paper, i.e. a resealable box, or plastic) to be of a size which will conveniently fit in a purse or in a pocket so that it can be easily carried by the user. Since the case may need to house 20, 30 or more applicators in order to handle a full treatment regimen, the size of each individual applicator needs to be fairly small. On the other hand, if the applicator is too small, it becomes difficult for some people to use. Thus, in preferred embodiments, the applicator of the invention has a length of from 3 to 6 cm, for example 3.5 to 6 cm, and a cross sectional height in the handle and blade region of from 0.8 to 1.2 mm. The neck portion then suitably has a lesser cross sectional height, in the range of from 0.5 to 0.7 mm.

The applicator is integrally formed from a material which provides two important characteristics: (1) the material should be non-absorbent with respect to the medication; and (2) the material should have sufficient flexibility and resilience to allow the neck to bend in response to very little pressure in order to provide a soft applicator feel. Suitable materials for this purpose are polyolefins, such as low density polyethylene and high density polyethylene, although other plastics that have flexibility sufficient to provide a "soft" touch are also suitable.

Figure 3:
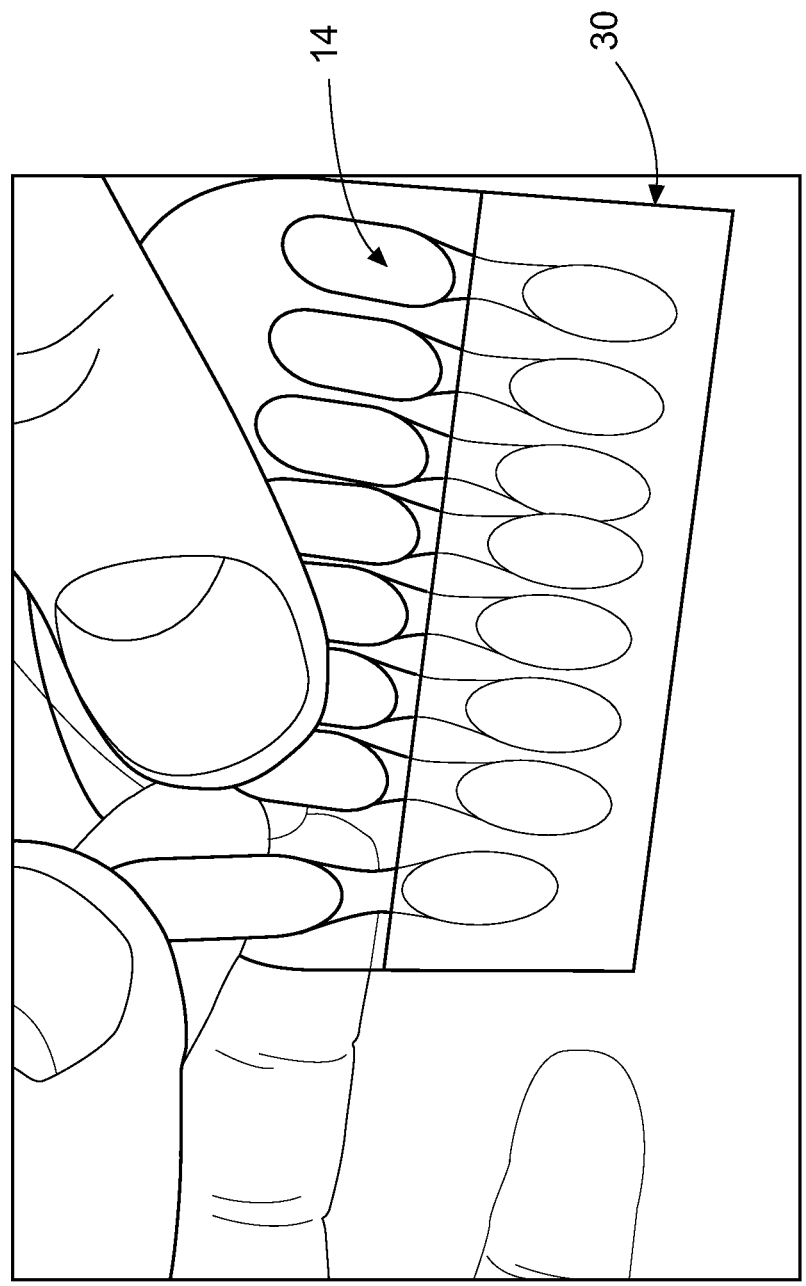
FIG. 3 shows a plurality of applicators on a carrier prior to use.

FIG. 3 shows a plurality of applicators 14 associated on a carrier 30 for placement in the kit of the invention. The number of applicators in the kit may suitably vary from a number sufficient to provide for a day or a few days of treatment (for example 5 to 10 applicators) so that the applicators can be used at times when there is limited ability for hand-washing, or may be a larger number sufficient to provide an applicator for each treatment in the container. In this latter case, the plurality of applicators is equal in number to the plurality of applications in the container. However, it is not necessary that all of the applicators be originally provided in the kit, so long as the case is of sufficient size to receive some plurality of applicators. The applicators may be unwrapped, individually wrapped, or provided on a carrier such as that shown in FIG. 3 in which they are associated as a group and protected from dust by an overwrap formed from a material such as oriented polyproylene, polythyelene terephthalate (PET) and low density polyolefins for example low density polyethylene. Transparency is desirable to allow visual confirmation of the number of applicators present, but is not required. When a single applicator 14 is removed from the carrier 30, the remaining applicator tips may remain protected in the carrier 30, which may be a reclosable sachet.

The medication in the container is provided in a fluid form. A fluid form of medication can be squeezed, dropped or pumped from the container and will have sufficient viscosity and/or surface tension to remain on the blade portion of the applicator even if it is tipped into an inverted position in preparation for application. Examples of fluid forms include without limitation gels, foams, creams, ointments, pastes, viscous liquids, and lotions.

The container can be a tube, a dropper or a pump dispenser, or any other type of container which can house the medication in a fluid form and dispense it onto the blade portion of the applicator.

The medication itself can be any type of medication that is routinely applied as a topical agent over multiple treatments. In specific embodiments, the medication contains an active ingredient used in the treatment of cold sores. Examples of specific active ingredients include without limitation antivirals such as penciclavir, famcyclovir, valcyclovir or acyclovir, numbing agents such as tetracaine, benzocaine, lidocaine, benzyl alcohol, camphor, and phenol; and other active agents used for this purpose such as Docosanol, zinc, lysine, phenol, and tannic acid.

To use the kit of the invention, a user takes a single applicator and applies to it an amount of medication consistent with the instructions. If desired, the surface 28 of the blade portion of the applicator may have markings thereon to assist in the dispensing of an appropriate amount of the medication. The specific positioning of these markings, if present will depend on the type of fluid form in which the medication is present, the concentration of the medication, and the size of the area to be treated. Once the medication is on the applicator, the applicator is used to apply the medication to the area to be treated. The applicator is then disposed of since there are additional applicators in the kit for use with subsequent applications. Thus, use of the kit overcomes the need to touch the cold sore or other area being treated with the fingers, the need to touch the medication with the fingers, the need to wash one's hands before or after the treatment, the risk of cross-contamination through repeat use of the same applicator. In addition, because of the kit format, the medication and the applicators are conveniently carried to be available for treatment initiation at the first sign of a cold sore (a tingle) or for maintaining the treatment regimen throughout a normal day. Thus, use of the kit improves the quality of care and enhances compliance in the treatment of cold sores.

The invention claimed is:

1. A kit for the treatment of medical conditions requiring topical application of a medication, said kit comprising a case having disposed therein: (a) a container of the medication, wherein the medication is in a fluid form and wherein the container contains sufficient medication for a plurality of applications; and (b) a plurality of applicators, said plurality of applicators being equal in number to the plurality of applications, wherein each applicator comprises an integrally formed handle portion and a flattened blade portion connected by a resilient neck portion, said resilient neck portion has a smaller cross section height than the handle portion and the blade portion such that the flattened blade portion can be deflected during use, and wherein the blade portion has a medication application surface that does not absorb the medication.

2. The kit of claim 1, wherein the plurality of applicators are individually wrapped.

3. The kit of claim 1, further comprising a mirror disposed within the case.

4. The kit of claim 3, wherein the plurality of applicators are individually wrapped.

5. The kit of claim 1, wherein each of the applicators has a length extending from one end of the handle to the opposite end of the flattened blade of from 3 to 6 cm, and wherein the cross sectional height of the resilient neck portion has is from 0.5 to 0.7 mm.

6. The kit of claim 5, wherein the applicators are formed from a polyolefin.

7. The kit of claim 6, wherein the polyolefin is low density polyethylene.

8. The kit of claim 7, wherein the handle portion of each applicator has a thumb depression formed in a surface thereof.

9. The kit of claim 1, wherein the medication is an antiviral agent.

10. The kit of claim 9, further comprising a mirror disposed within the case.

11. The kit of claim 9, wherein each of the applicators has a length extending from one end of the handle to the opposite end of the flattened blade of from 3 to 6 cm, and wherein the resilient neck portion has a cross-section thickness of from 0.5 to 0.7 mm.

12. The kit of claim 11, wherein the applicators are formed from a polyolefin.

13. The kit of claim 12, wherein the polyolefin is low density polyethylene.

14. The kit of claim 13, wherein the handle portion of each applicator has a thumb depression formed in a surface thereof.

15. The kit of claim 9, wherein the antiviral agent is penciclovir.

16. The kit of claim 15, further comprising a mirror disposed within the case.

17. The kit of claim 15, wherein each of the applicators has a length extending from one end of the handle to the opposite end of the flattened blade of from 3 to 6 cm, and wherein the cross-sectional height of the neck portion is from 0.5 to 0.7 mm.

18. The kit of claim 17, wherein the applicators are formed from a polyolefin.

19. The kit of claim 18, wherein the polyolefin is low density polyethylene.

20. The kit of claim 19, wherein the handle portion of each applicator has a thumb depression formed in a surface thereof.

21. The kit of claim 9, wherein the antiviral agent is acyclovir.

22. The kit of claim 21, further comprising a mirror disposed within the case.

23. The kit of claim 21, wherein each of the applicators has a length extending from one end of the handle to the opposite end of the flattened blade of from 3 to 6 cm, and wherein the cross sectional height of the resilient neck portion is from 0.5 to 0.7 mm.

24. The kit of claim 23, wherein the applicators are formed from a polyolefin.

25. The kit of claim 24, wherein the polyolefin is low density polyethylene.

26. The kit of claim 25, wherein the handle portion of each applicator has a thumb depression formed in a surface thereof.

* * * * *